United States Patent [19]

Coleman et al.

[11] Patent Number: 5,331,962
[45] Date of Patent: Jul. 26, 1994

[54] ULTRASOUND SYSTEM FOR CORNEAL BIOMETRY

[75] Inventors: Donald J. Coleman, Haworth, N.J.; Ronald H. Silverman, Brooklyn, N.Y.

[73] Assignee: Cornell Research Foundation Inc., Ithaca, N.Y.

[21] Appl. No.: 48,786

[22] Filed: Apr. 16, 1993

[51] Int. Cl.[5] ............................................. A61B 8/10
[52] U.S. Cl. ................... 128/660.09; 128/661.06
[58] Field of Search ................ 128/661.06, 660.09, 128/660.08, 660.06

[56] References Cited

U.S. PATENT DOCUMENTS

| | | | |
|---|---|---|---|
| 3,404,936 | 10/1968 | Bennett et al. | 351/6 |
| 3,805,596 | 4/1974 | Klahr | 128/660.09 |
| 4,167,180 | 9/1979 | Kossoff | 128/660.09 |
| 4,455,872 | 6/1984 | Kossoff et al. | 128/660.09 |
| 4,484,569 | 11/1984 | Driller et al. | 128/660 |
| 4,508,121 | 4/1985 | Myers | 128/639 |
| 4,546,773 | 10/1985 | Kremer et al. | 128/660 |
| 4,564,018 | 1/1986 | Hutchison et al. | 128/660 |
| 4,817,432 | 4/1989 | Wallace et al. | 73/602 |
| 4,858,124 | 8/1989 | Lizzi et al. | 364/413.01 |
| 4,930,512 | 6/1990 | Henricksen et al. | 128/661.06 |
| 4,932,414 | 6/1990 | Coleman et al. | 128/660.09 |
| 5,029,587 | 7/1991 | Baba et al. | 128/660 |
| 5,056,522 | 10/1991 | Matsumura et al. | 128/646 |

OTHER PUBLICATIONS

"Ultrasonographic, Three-Dimensional Scanning for Determination of Intraocular Tumor Volume", Hansen et al., Acta Ophthalmologica, 1991, 69, pp. 178–186.
"Ultrasonography of the Eye and Orbit", Coleman et al., Lea & Febiger, 1977, pp. 51–88.
"A 100 MHz B-Scan Ultrasound Backscatter Microscope", Sherar et al., Ultrasonic Imaging 11, 95–105, (1989).

Primary Examiner—William E. Kamm
Assistant Examiner—George Manuel
Attorney, Agent, or Firm—Perman & Green

[57] ABSTRACT

An ultrasonic biometer images an eye structure and enables measurement of a cornea's thickness at various points about the cornea's surface curvature. The biometer employs a liquid bath in contact with the corneal surface and includes a curved track positioned above the liquid bath, the curved track having a path that closely approximates the surface curvature of the corneal surface. An ultrasonic transducer (having a central axis) is movably mounted by a connector structure along the track and is positioned in communication with the liquid bath. The connector structure operates to maintain the central axis of the ultrasonic transducer perpendicular to a tangent drawn to the curved track, at a plurality of locations along the track. When the connector structure is moved along the curved track, it enables an ultrasonic beam, generated by the transducer, to interrogate areas of the corneal surface, with the angle of incidence of the beam being substantially orthogonal to the surface.

6 Claims, 2 Drawing Sheets

ULTRASOUND SYSTEM FOR CORNEAL BIOMETRY

FIELD OF THE INVENTION

This invention relates to ultrasound imaging systems, and more particularly, to an ultrasound imaging system particularly designed for imaging and measuring the thickness of a patient's cornea.

BACKGROUND OF THE INVENTION

Surgical alteration of the shape of a patient's cornea to improve visual acuity has been practiced for a number of years. In such surgery, radial cuts are made into the surface of the cornea so as to alter its external curvature and, thus, its focal distance. Such surgery is termed radial keratotomy. More recently, excimer lasers have been employed to ablate sections of the patient's cornea to modify its optical properties. Recent advances in excimer laser keratectomy provide a surgical precision that challenges the ability to localize corneal pathologies with a high degree of accuracy. Before employing such laser-based surgical procedures, it is vital to know with precision, the thickness of individual corneal layers so as to assure the application of proper levels of laser power.

The prior art teaches a variety of techniques for imaging a cornea's structure. In U.S. Pat. No. 3,404,936 to Bennett et al, an ophthalmic instrument is described that enables measurement of the curvature of the cornea. The Bennett et al instrument is mounted on a curved support and enables a number of optical readings to be taken so as to chart the cornea's curvature.

Another method for determining corneal thickness and curvature is termed Pachymetry and involves the use of an ultrasonic probe to provide an A-scan image of various portions of a corneal surface. U.S. Pat. No. 4,817,432 to Wallace et al., U.S. Pat No. 4,546,773 to Kremer et al., U.S. Pat. No. 4,508,121 to Myers, U.S. Pat. No. 5,056,522 to Matsumura et al. and U.S. Pat. No. 5,029,587 to Baba et al., all describe various Pachymeter systems that provide A-scan corneal imaging and thickness measurements. Wallace et al employ a hand held probe, whereas the remaining patents show fixed ultrasonic transducers that provide ultrasonic corneal thickness measurements. U.S. Pat. No. 4,564,018 to Hutchison et al. and U.S. Pat. No. 4,930,512 to Henrikson et al. each disclose details of hand-held ultrasonic probes that enable ocular measurements to be obtained. The probes described by Hutchison et al. and Henrikson et al. require direct application of the probe structure to either a corneal surface or to an eyelid.

The prior art also includes teachings of the use of scanned ultrasonic transducers for the production of B-scan presentations of ocular structures. U.S. Pat. No. 4,484,569 to Driller et al. shows the provision of first and second transducers that are coaxially mounted. The first transducer enables both A and B-scan presentations to be obtained of an ocular structure, with the second transducer being employed for therapeutic use. U.S. Pat. 4,858,124 to Lizzi et al. also describes a fixed ultrasonic transducer whose beam is scanned and thereby creates a pie-shaped B-scan for ocular imaging (see FIG. 4).

U.S. Pat. No. 4,932,414 to Coleman et al. shows a B-scan ultrasonic transducer that is angularly mounted about a fixed axis therapeutic transducer. The B-scan transducer is rotatable about the therapeutic transducer and creates a pie-shaped sector scan and is movable so as to produce multiple B-scan presentations.

Ultrasonic B-scan presentations have also been employed to image intraocular tumor volumes by three-dimensionally scanning an ultrasonic transducer head. In one such system a conventional sector scanner is rotated around its axis. (See Hansen et al "Ultrasonographic, Three-dimensional Scanning for Determination of Intraocular Tumor Volume", Acta Ophthalmologica, 1991, 69, pages 178-186. Sherat et al have also disclosed the use of a B-scan ultrasound microscope for producing B-scan images of ocular structures (See Ultrasonic Imaging, Volume 11, pages 95-105, 1989). In the Sherat et al structure, a transducer is mounted in a liquid-filled tank and is moved about the surface of the tank so as to obtain an image of a specimen that is positioned within the tank.

Coleman et al. in "Ultrasonography of the Eye and Orbit", Lea and Febiger, 1977 pages 51-88, describe a number of ultrasonic systems that provide both A, B, and M mode systems. At pages 65-69, various scan pattern are considered, i.e. linear, sector, arc, and compound combinations thereof. Coleman et al. also indicate that the most useful patterns are those in which the ultrasonic beam is perpendicularly aligned with reflective tissue surfaces, in that the echoes travel directly back to the transducer rather than being redirected along misaligned axes. Coleman et al. do not specifically teach how to obtain such perpendicular alignment over a complete corneal surface.

As is evident from the above, ultrasound has been widely employed to image both ocular and corneal structures. However, with the onset of excimer laser kerotectomy, extraordinarily precise measurements of corneal thickness over a cornea's entire surface are required. At a minimum, a highly accurate B-scan image of the corneal structure must be obtained. Furthermore, it is important to be able to specifically localize areas of opacity in the cornea. In order to achieve optimum imaging of corneal structures, the reflected signals must be as noise free as possible and spurious reflections must be minimized. Due to the highly reflective properties of the corneal surface, such high quality signals are difficult to achieve.

Accordingly, it is an object of this invention to provide an improved ultrasound scanner for obtaining ocular images.

It is another object of this invention to provide an improved ultrasound scanner that is able to achieve highly accurate corneal thickness measurements.

It is still another object of this invention to provide an improved ultrasound ocular scanner which provides enhanced ocular images without requiring direct transducer contact with the cornea.

SUMMARY OF THE INVENTIONS

An ultrasonic biometer images an eye structure and enables measurement of a cornea's thickness at various points about the cornea's surface curvature. The biometer employs a liquid bath in contact with the corneal surface and includes a curved track positioned above the liquid bath, the curved track having a path that closely approximates the surface curvature of the corneal surface. An ultrasonic transducer (having a central axis) is movably mounted by a connector structure along the track and is positioned in communication with the liquid bath. The connector structure operates to maintain the central axis of the ultrasonic transducer perpendicular to a tangent drawn to the curved track, at a plurality of locations along the track. When the connector structure is moved along the curved track, it enables an ultrasonic beam, generated by the transducer, to interrogate areas of the corneal surface, with the angle of incidence of the beam being substantially orthogonal to the surface.

DETAILED DESCRIPTION OF THE INVENTION

Figure 1:
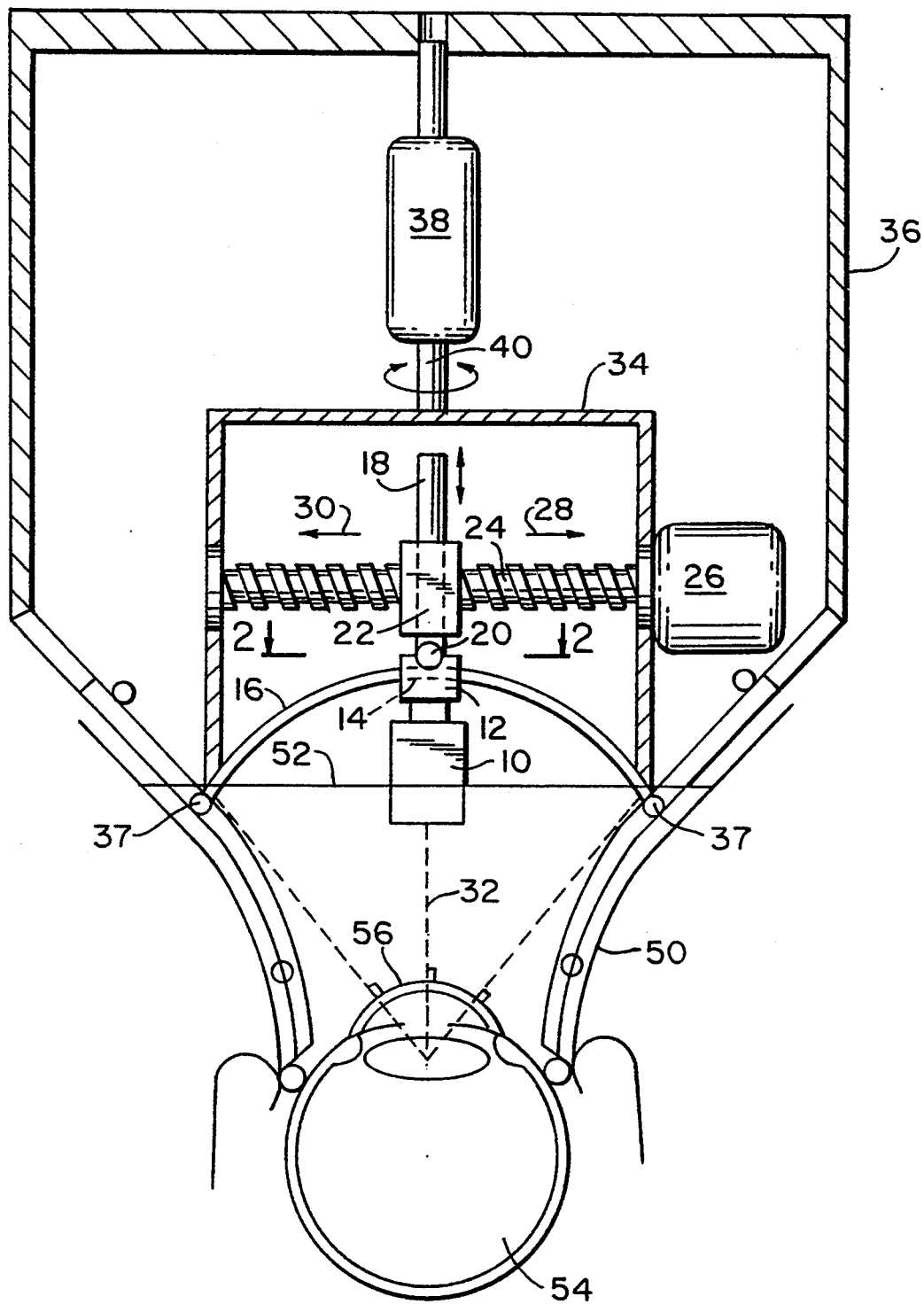
FIG. 1 is a side schematic view of a structure that incorporates the invention.

Referring to FIG. 1, an ultrasonic transducer 10 is fixedly mounted to a carriage 12. Carriage 12 is provided with a curved slot 14 (shown dotted) which mates with a curved track 16. Carriage 14 is connected to a shaft 18 via a pivot mount 20. Shaft 18 is vertically movable within a follower 22 which is, in turn, movably mounted on worm gear 24. Worm gear 24 is driven by a reversible motor 26. When motor 26 is energized, worm gear 24 will rotate either clockwise or counterclockwise, as the case may be, causing follower 22 to track along the length of worm gear 24 in one of the directions shown by arrows 28 or 30. The movement of follower 22 is transmitted to carriage 12 by a shaft 18 and pivot mount 20. As a result, carriage 12 moves along curved track 16 and causes ultrasonic transducer 10 to move in a like fashion.

Carriage 12 is mounted on curved track 16 such that transducer 10 remains perpendicular to a tangent to curved track 16 as it moves along track 16. An important feature of this invention is that the curvature of track 16 is designed to closely follow (if not duplicate), the curvature of an eye's cornea. Thus, as ultrasonic transducer 10 is moved along track 16 by carriage 12, its beam 32 will always be substantially perpendicular to the surface of a cornea being examined, thereby enabling a precise thickness measurements thereof to be obtained. The perpendicularity of beam 32 to the corneal surface also assures that diverse reflections from the corneal surface are minimized, thus, maximizing the sensed reflected signal.

Motor 26 and worm gear 24 are both mounted for rotation within a frame 34. Frame 34 is mounted for rotation within a housing 36 and is enabled to rotate by the action of a motor 38 through axle 40. Frame 34 rides in a bearing surface 37 within housing 36. Curved track 16 is also fixedly mounted to frame 34 and is rotatable therewith. Thus, the rotation of motor 38 causes frame 34 and curved track 16 to rotate about axle 40.

Housing 36 may either be designed to be hand-held or, in the alternative, to be mounted on an externally positioned frame which enables its vertical and horizontal adjustment.

Figure 2:
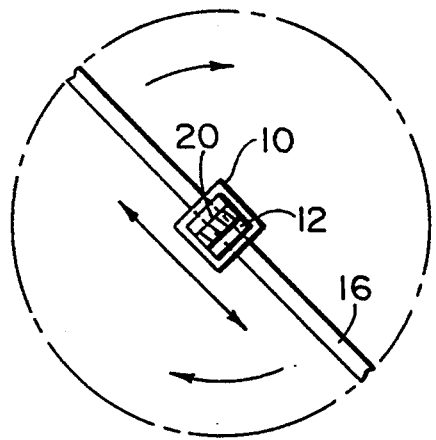
FIG. 2 is a plan view of the track portion of the structure of FIG. 1 taken along line 2—2.

Referring to FIG. 2, track 16 is shown in plan view, with carriage 12 and transducer 10 mounted thereon. The action of worm gear 24 (not shown in FIG. 2) causes transducer 10 to move along the length of track 16, while the action of motor 38 causes track 16 to rotate either clockwise or counter clockwise, as the case may be. In this manner, transducer 10 can be scanned over an entire corneal surface at any angular orientation, so as to achieve a complete mapping of cornea's surface and thickness. As aforesaid, at all scan positions the ultrasound beam generated by transducer 10 is perpendicular to the cornea's surface.

Returning to FIG. 1, an eye cup 50 is positioned against a patient's eye so as to provide a sealed container for a liquid bath 52. The distal opening of eyecup 50 bears upon the sclera of eye 54 and provides a bottom seal to prevent escape of liquid bath 52. The lower portion of case 36 fits within eye cup 50 and enables transducer 10 to be immersed in liquid bath 52. As above indicated, the curvature of track 16 is designed to match the curvature of cornea 56 of eye 54 so that as transducer 10 is moved therealong, its beam 32 always remains perpendicular to the surface of cornea 56. Thus, by appropriate operation of motors 26 and 38, the entire surface of cornea 56 can be accurately mapped, simply by rotating the position of frame 34 in a plurality of discrete steps and, at each step, causing motor 26 to move carriage 22 from one to another extremity of worm gear 24.

Figure 3:
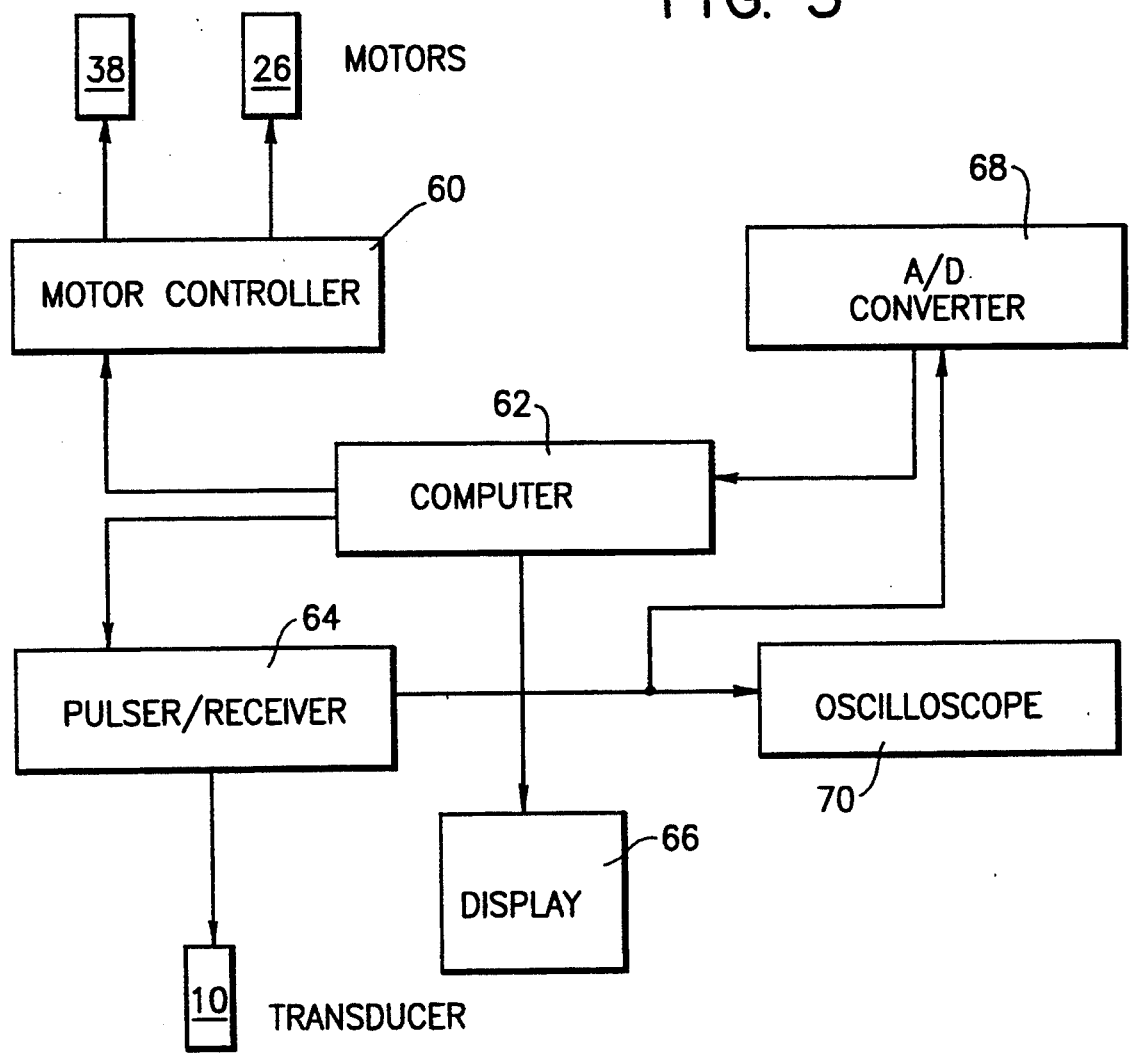
FIG. 3 is a block diagram of the circuitry employed to control the operation of the invention.

In FIG. 3, a block diagram is illustrated of the electronics required to operate the ultrasound system of FIG. 1. Motors 26 and 38 are connected to a motor controller 60 whose operation is, in turn, controlled by computer 62. Transducer 10 is connected to a pulser/receiver circuit 64 which is, in turn, controlled by computer 62. Display 66 provides a B-scan display of cornea 56 after the signals from transducer 10 have been processed by pulser/receiver 64, passed to A/D convertor 68 and thence into computer 62. An oscilloscope 70 may be employed with the system to enable a user to obtain precise measurements of corneal thicknesses from a displayed A-scan image of specific scan points of cornea 56.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. An ultrasonic biometer for imaging a structure of a cornea, said biometer comprising:

means for establishing a liquid bath in contact with a surface of said cornea;

curved track means having a path that approximates a surface curvature of said cornea;

ultrasonic transducer means having a central axis;

connector means for movably mounting said ultrasonic transducer means on and for movement along said curved track means so as to position said transducer means in communication with said liquid bath, said connector means operative, upon movement of said ultrasonic transducer means along said curved track means, to maintain said central axis of said ultrasonic transducer means perpendicular to tangents to said curved track means at a plurality of locations along said curved track means; and means for causing said connector means to move along said curved track means so as to enable an ultrasonic signal transmitted by said ultrasonic transducer means to interrogate areas of said cornea.

2. The ultrasonic biometer as recited in claim 1 further comprising:

means for rotatably repositioning said curved track means so as to alter an angular relationship between said curved track means and a bisector of said cornea to enable said connector means to move along said curved track means and along a different bisector orientation of said cornea.

3. The ultrasonic biometer as recited in claim 2 wherein said connector means comprises a carriage connected to said ultrasonic transducer means, said carriage provided with a pathway that mates with said curved track means at all positions therealong and maintains said transducer means substantially perpendicular to said tangents at said plural locations along said curved track means.

4. The ultrasonic biometer as recited in claim 3 further comprising:
   a worm gear mounted parallel to a projection of said curved track means;
   motor means for rotating said worm gear; and
   follower means mounted on said worm gear and connected to said carriage, said follower means being movable along said worm gear upon a rotation thereof, said follower means causing said carriage to move along a length of said curved track means in accordance with rotation of said worm gear.

5. An ultrasonic biometer as recited in claim 4 further comprising:
   a frame for rigidly mounting said worm gear and said curved track means in alignment; and
   motor means for rotating said frame so as to rotate said worm gear and curved track means in coincidence, whereby said worm gear continually remains parallel to said projection of said curved track means.

6. The ultrasonic biometer as recited in claim 5 wherein said carriage is connected to said follower means by a slidable shaft, said shaft being slidable in said follower means so as to enable said carriage to move along said curved track means without requiring adjustment of the distance between said carriage and said follower means.

* * * * *